United States Patent [19]

Kwantes

[11] 4,308,405
[45] Dec. 29, 1981

[54] PREPARATION OF BISPHENOLS

[75] Inventor: Ariën Kwantes, Amsterdam, Netherlands

[73] Assignee: Shell Oil Company, Houston, Tex.

[21] Appl. No.: 922,022

[22] Filed: Jul. 5, 1978

[51] Int. Cl.³ .................... C07C 39/12; C07C 39/16
[52] U.S. Cl. .................................... 568/727; 568/728
[58] Field of Search ........................................ 568/727

[56] References Cited

U.S. PATENT DOCUMENTS

| 2,730,552 | 1/1956 | Williamson | 568/727 |
| 2,775,620 | 12/1956 | Williamson | 568/727 |
| 2,791,616 | 5/1957 | Luten | 568/727 |
| 3,242,220 | 3/1966 | Apel et al. | 568/727 |

Primary Examiner—Werren B. Lone

[57] ABSTRACT

An improved continuous process for preparing bisphenols from phenols and carbonyl compounds in the presence of an acidic ion-exchange resin is described. The improvement comprises recycling a portion of the stream containing bisphenol to the reaction zone before the bisphenol is recovered therefrom.

8 Claims, 1 Drawing Figure

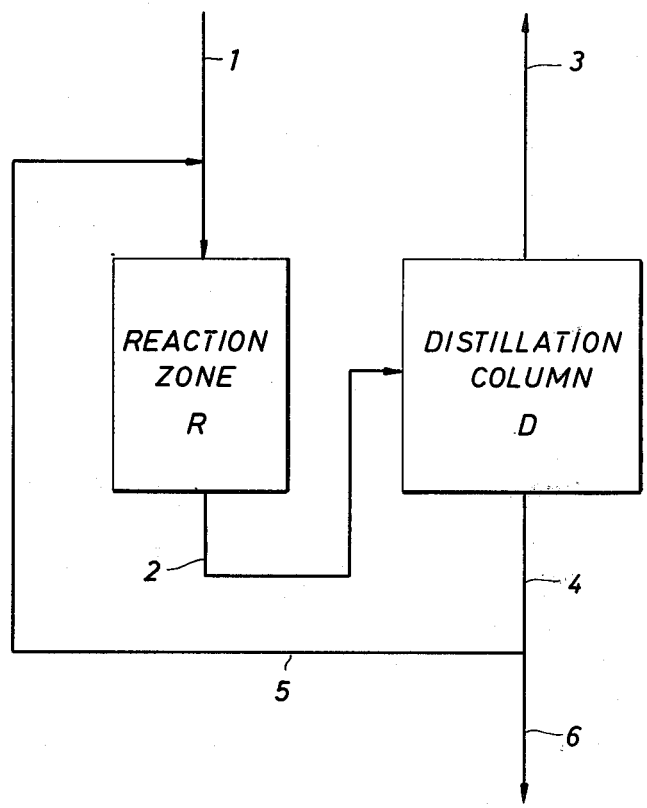

PREPARATION OF BISPHENOLS

BACKGROUND OF THE INVENTION

It is known to prepare bisphenols, e.g., Bisphenol A, by continually reacting, in a reaction zone, at least 2 moles of a phenol with a carbonyl compound in the presence of an acidic ion-exchange resin. The reaction zone effluent is a mixture of unreacted carbonyl compound, phenol, water, bisphenol and reaction by-products. Some of the bisphenol and phenol may be in the form of an adduct. It is possible to remove all of the carbonyl compound and water and a part of the phenol from the reaction zone effluent and to recover the bisphenol from the remainder of the reaction zone effluent, e.g., see U.K. Pat. No. 883,391.

It has now surprisingly been found that the concentration of bisphenol in the remainder of the reaction zone effluent may be substantially increased without adversely effecting the properties of the acidic ion-exchange resin or of the recovered bisphenol if a part of the remainder of the reaction effluent is recycled to the reaction zone.

SUMMARY OF THE INVENTION

The present invention is directed to an improved process for preparing bisphenols from a phenol and a carbonyl compound in the presence of an acidic ion-exchange resin wherein a portion of the reaction zone effluent containing bisphenol is recycled to the reaction zone before the bisphenol is recovered therefrom.

DESCRIPTION OF THE DRAWING

The drawing is a schematic diagram of a preferred process embodiment of the present invention.

DESCRIPTION OF PREFERRED EMBODIMENTS

The present invention is preferably concerned with a continuous process for the preparation of bisphenols comprising reacting, in a reaction zone, at least two moles of a phenol with a carbonyl compound in the presence of an acidic ion-exchange resin, separating the reaction zone effluent into two streams, the first stream comprising unreacted carbonyl compound, water and phenol and the second stream comprising bisphenol, reaction by-products and phenol and recovering bisphenol from the second stream, characterized in that a part of the second stream is recycled to the reaction zone before the bisphenol is recovered therefrom.

The reaction zone may comprise a single reactor or two or more reactors in series. In the case of a multi-reactor reaction zone, suitably all of the phenol is fed to the first reactor and the carbonyl compound is either fed all to the first reactor or divided between the second and possibly further reactors, if any.

As stated above, the reaction zone effluent is separated into two streams. This separation is suitably achieved by the removal, by distillation, of all of the unreacted carbonyl compound and water and a part of the phenol. The reaction zone effluent, depending on the temperature thereof and the pressure used, may be heated or cooled to effect this separation. In the case of a distillation column, the temperature thereof is suitably maintained at a temperature of from 130° to 220° C. and a pressure sufficient to completely separate the carbonyl compound and water and a part of the phenol from the reactor zone effluent. In practice the amount of phenol removed is the minimum amount removed during the complete removal of the unreacted carbonyl compound and water. The stream thus obtained, which preferably amounts to from 1 to 10 %w of the reaction zone effluent, may be worked-up and the unreacted carbonyl compound and phenol recycled.

The residue of the separation, i.e., the second stream, comprises bisphenol, reaction by-products and phenol. Suitably the amount of phenol in this stream is from 4 to 15 moles per mole of bisphenol. An important feature of the present invention is the recycling of a part of this second stream to the reaction zone. In a preferred embodiment of the present invention the recycle ratio, which is the ratio by weight, of the recycle stream to the remainder of the second stream, is in the range of from 0.2:1 to 4:1, with recycle ratios in the range of from 0.5:1 to 2:1 being particularly preferred.

The bisphenol may be recovered from the remainder of the second stream by conventional techniques such as by the removal of the phenol therefrom by evaporation. The bisphenol may also be recovered by crystallization.

Suitable acidic ion-exchange resins for use in the present invention are those whose structure is such so as to render the resin insoluble in the reaction medium. Preferred resins contain a plurality of sulphonic acid groups. Such sulphonated ion-exchange resins may be sulphonated styrene-divinylbenzene copolymers or sulphonated phenolformaldehyde resins. The sulphonated resins are commercially available in a dry or water swollen form and either form may be used in the process. Specific examples of suitable resins are Amberlite IR-120H, Amberlyst 15H⊕, Dowex 50-X-4, Dowex MSC-1H, Duolite C-26, Permutit QH, Chempro C-20 and Imac C8P/H+ (Amberlite, Amberlyst, Dowex, Duolite, Permutit, Chempro and Imac are registered Trade Marks). The exchange capacity of the acidic resin is preferably at least 2.0 meq H+/g of dry resin, with exchange capacities in the range of from 3.0 to 5.5 meq H+/g of dry resin being particularly preferred.

The acidic ion-exchange resin may be partially modified with a compound having an acidic reacting group and a mercaptan group. Modification may be carried out by either partially esterifying the resin with a mercapto alcohol, e.g., see U.K. Pat. No. 937,072, or by partially neutralizing the resin with an alkyl mercaptoamine such as thiothanolamine, e.g., see Belgian Pat. No. 589,727 and U.K. Pat. No. 1,183,564, precursors of alkyl mercaptoamines such as thiazolidines, e.g., see U.K. Pat. No. 1,361,430, cyclomercaptoamines and mercaptoaminocarboxylic acid, as well as thiazolidine precursors of the latter. Suitably from 2 to 25%, preferably from 5 to 20%, of the acidic groups are modified. As an alternative to such modification, the reaction may be carried out in the presence of a dissolved sulphur comound as promotor; examples include alkyl mercaptans such as methyl and ethylmercaptan and mercapto-substituted aliphatic carboxylic acids such as 3-mercapto propionic acid.

The reactor may be filled with the acidic ion-exchange resin by any known technique. Such techniques include adding the desired amount of dry resin, water-wet resin or slurry of the resin to the reactor. The resin bed is suitably fixed and is usually supported on one or more grids.

Suitable phenols for use in the present invention should have a reactive hydrogen atom, preferably in the para-position relative to the phenolic hydroxyl group. Such phenols may be substituted by one or more alkyl groups, e.g. lower alkyl groups such as methyl or tertiary butyl groups; halogen atoms, such as chlorine atoms, or other non-interfering substituents. Specific examples of phenols include ortho- and meta-cresol; 2,6-dimethylphenol; ortho-sec.butyl phenol; ortho-tert. butyl-phenol; 2,6-di-tert.butylphenol; 1,3,5-xylenol; tetramethylphenol; 2-methyl-6-tert.butylphenol; ortho-phenylphenol; ortho- and meta-chlorophenol; ortho-bromophenol; 6-chloro-orthocresol and 2,6-dichlorophenol. Phenol itself is the preferred phenol.

The carbonyl compounds used in the process may be aldehydes or ketones with the latter being preferred. Preferred ketones are those having at least one methyl group alpha to a carbonyl group or are cyclic ketones. Specific examples include acetone, methyl ethyl ketone, methyl propyl ketone, acetophenone, methyl vinyl ketone and cyclohexanone. Acetone is the preferred ketone. The present invention is particularly suitable for the preparation of 2,2-bis(4-hydroxyphenyl) propane, Bisphenol A.

The molar ratio of phenol to carbonyl compound is at least 2 with a stoichiometric excess of phenol being preferred. Suitable molar ratios are from 3:1 to 50:1, with molar ratios of from 10:1 to 30:1 being preferred. The optimum ratio depends inter alia on reaction conditions, e.g. temperature of reaction and desired conversion.

The reaction temperature in the reactor zone may vary between wide limits with a reaction temperature in the range of from 30° C. to 120° C. being suitable and a reaction temperature in the range of from 40° C. to 100° C. being preferred.

The reaction time in the reactor zone may also vary between limits and depends inter alia on reaction temperature. For example an average total contact time of from 3 minutes to 10 hours may be used. The liquid hourly space velocity (LHSV) of the feed may vary between wide limits with velocities in the range of from 0.2 to 40 liters feedstream liter catalyst$^{-1}$.hour$^{-1}$ being suitable.

The bisphenols so prepared may be used in a variety of applications such as to prepare anti-oxidants, epoxy resins and polycarbonate resins.

The process will now be illustrated by reference to the accompanying drawings which is a schematic diagram of a preferred embodiment of the present invention.

In this embodiment a feedstream 1 comprising the phenol and the carbonyl compound is continuously fed to the reaction zone R comprising a fixed bed of an acidic ion-exchange resin. The reaction zone R effluent stream 2 is continuously withdrawn and fed to a distillation column D from which an overhead stream 3 comprising all of the carbonyl compound and water and a part of the phenol is continuously withdrawn and worked-up. A bottom stream 4 comprising bisphenol, reaction byproducts and phenol is continuously withdrawn and a part thereof recycled as stream 5 to the reaction zone R. The remaining part thereof, stream 6, is worked-up to recover the bisphenol therefrom.

The following examples illustrate the instant process for preparing bisphenols and are for the purpose of illustration only and are in no way intended to limit the invention to the particular schemes illustrated. Modifications within the spirit and scope of the present invention will become apparent to those skilled in the art. Parts and percentages are by weight unless otherwise noted.

EXAMPLE 1

A tubular reactor (150 cm long; 2 cm internal diameter), connected in series with a distillation column (150 cm long; 2 cm internal diameter), was partially filled with an aqueous slurry containing 130 g (dry basis) of a sulphonated styrene/divinylbenzene acidic ion-exchange resin which had been partially neutralized (10%) with thioethanolamine having an exchange capacity of 4.25 meq H$^+$/g dry resin, and the water drained-off to form a fixed bed of resin. The reactor was maintained at a temperature of 65° C. and the distillation column was maintained at a bottom temperature of 194° C.

A feedstream comprising phenol and acetone was continuously passed through the reactor at a liquid hourly space velocity of 5 liter.-liter catalyst$^{-1}$.hour$^{-1}$ and the reactor effluent continuously withdrawn and fed to the distillation column from which a top stream (distillate stream) and a bottom stream (recovery stream) were continuously withdrawn. After 120 hours of operation the acetone conversion, on intake, was 52%, and the streams had the following compositions.

|  | Reactor feedstream (1750 g/h) % w | Reactor effluent (1750 g/h) % w | Distillate stream (48 g/h) % w | Recovery stream (1702 g/h) % w |
| --- | --- | --- | --- | --- |
| acetone | 3.94 | 1.9 | 69.1 | — |
| phenol | 96.06 | 89.36 | 7.7 | 91.7 |
| diphenylol propane | — | 8.0 | — | 8.2 |
| water | — | 0.64 | 23.2 | — |
| by-products | — | 0.1 | — | 0.1 |

The recovery stream was worked-up by evaporating the phenol therefrom and the recovered diphenylol propane (DPP) had an ortho/para DPP to para/para DPP ratio of 2.1/97.9 and a color of 54 Hazen. The amount of phenol that had to be removed by evaporation from the recovery stream was 11.29 g/g of diphenylol propane.

EXAMPLE 2

Example 1 was repeated with the difference that 60%w of the bottom stream from the distillation column was continuously recycled (a recycle ratio of 1.5:1) to the reaction zone. The liquid hourly space velocity of the reactor feedstream (fresh feedstream plus recycle stream) was 6 liter.liter catalyst$^{-1}$.hour$^{-1}$. After 120 hours of operation the acetone conversion, on intake, was 51%, and the streams had the following compositions.

|  | Reactor feedstream (2064 g/h) % w | Reactor effluent (2064 g/h) % w | Distillate stream (48 g/h) % w | Recycle stream (1217 g/h) % w | Recovery stream (799 g/h) % w |
| --- | --- | --- | --- | --- | --- |
| acetone | 3.3 | 1.68 | 71 | — | — |
| phenol | 86.7 | 81.1 | 7 | 83 | 83 |
| diphenylol propane | 9.9 | 16.5 | — | 16.8 | 16.8 |
| water | — | 0.52 | 22 | — | — |
| by-products | 0.1 | 0.2 | — | 0.2 | 0.2 |

The recovered diphenylol propane had an ortho/para DPP to para/para DPP ratio of 2.2/97.8 and a color of 54 Hazen. The amount of phenol that had to be removed by evaporation from the recovery stream was 4.9 g/g of diphenylol propane.

What I claim is:

1. A continuous process for the preparation of 2,2-bis(4-hydroxyphenyl)propane comprising reacting, in a reaction zone, at a temperature from about 30° to about 120° C., at least two moles of phenol with acetone in the presence of an acid ion-exchange resin having an exchange capacity of at least 2.0 meq H+/g of dry resin, separating the reaction zone effluent into two streams, the first stream comprising unreacted acetone, water and phenol and the second stream comprising 2,2-bis(4-hydroxyphenyl)propane, reaction by-products and phenol and recovering 2,2-bis(4-hydroxyphenyl)propane from the second stream, wherein a part of the second stream is recycled to the reaction zone before the 2,2-bis(4-hydroxyphenyl)propane is recovered therefrom.

2. The process of claim 1 wherein the recycle ratio is from 0.2:1 to 4:1.

3. The process of claim 1 wherein the reaction zone effluent is separated into two streams by distillation.

4. The process of claim 1 wherein the first stream comprises from 1 to 10%w of the reaction zone effluent.

5. The process of claim 1 wherein the acidic ion-exchange resin is a sulphonated styrene-divinyl copolymer.

6. The process of claim 1 wherein the molar ratio of phenol to acetone is from 10:1 to 30:1.

7. The process of claim 1 wherein the reaction temperature is from 40° C. to 100° C.

8. The process of claim 5 wherein the ion-exchange resin has been partially neutralized with an alkyl mercaptoamine.

* * * * *